(12) United States Patent
Young et al.

(10) Patent No.: US 8,501,483 B2
(45) Date of Patent: Aug. 6, 2013

(54) METHOD OF ASSESSING CANCER STATUS IN A BREAST CANCER PATIENT

(75) Inventors: Leonie Young, Dublin (IE); Marie McIlroy, Dublin (IE); Arnold Hill, Dublin (IE); Peadar O'Gaora, Dublin (IE); Sarah Earley, Dublin (IE); Damian McCartan, Dublin (IE)

(73) Assignees: University College Dublin, National University of Ireland, Dublin, Dublin (IE); The Royal College of Surgeons in Ireland, Dublin (IE)

( * ) Notice: Subject to any disclaimer, the term of this patent is extended or adjusted under 35 U.S.C. 154(b) by 0 days.

(21) Appl. No.: 12/937,439

(22) PCT Filed: Apr. 14, 2009

(86) PCT No.: PCT/IE2009/000015
§ 371 (c)(1),
(2), (4) Date: Jan. 7, 2011

(87) PCT Pub. No.: WO2009/144690
PCT Pub. Date: Dec. 3, 2009

(65) Prior Publication Data
US 2011/0097806 A1    Apr. 28, 2011

Related U.S. Application Data

(60) Provisional application No. 61/044,549, filed on Apr. 14, 2008, provisional application No. 61/044,546, filed on Apr. 14, 2008.

(51) Int. Cl.
*G01N 33/48* (2006.01)
*G01N 33/574* (2006.01)

(52) U.S. Cl.
USPC ......... 436/64; 436/63; 436/86; 435/4; 435/29

(58) Field of Classification Search
USPC .............................. 436/63, 64, 86; 435/4, 29
See application file for complete search history.

(56) References Cited

U.S. PATENT DOCUMENTS

| | | | |
|---|---|---|---|
| 2005/0100933 A1* | 5/2005 | Erlander et al. | 435/6 |
| 2009/0304697 A1* | 12/2009 | Paik et al. | 424/138.1 |

FOREIGN PATENT DOCUMENTS

WO    2005/010180    *    2/2005

OTHER PUBLICATIONS

Castets et al., Molecular Brain Research, 46:208-216 (1997). "Transcriptional regulation of the human S100-beta gene."
Donato et al., Biochimica et Biophysica Acta, 1793:1008-1022 (2009). "S100-beta's double life: Intracellular regulator and extracellular signal."
Funahashi et al., Journal of Surgical Oncology, 68(1):25-29 (1998). "Different distributions of immunoreactive S100-alpha and S100-beta protein expression in human breast cancer."
Makiyama et al., Oncology Reports, 13(4):673-679 (2005). "Aberrant expression of HOX genes in human invasive breast carcinoma."
McCartan et al., European Journal of Surgical Oncology, 34(10):1197 (2008). "A role for the developmental protein HOXc11 as a mediator of endocrine resistance in breast cancer."
McCartan et al., Irish Journal of Medical Science, 177(Suppl 1):S14 (2008). "The developmental protein hoxc11 mediates altered differentiation in breast cancer stem cells."
Zhang et al., Journal of Cellular and Molecular Medicine, 11(2):299-306 (2007). "HOXC6 and HOXC11 increase transcription of S100 beta gene in BrdU-induced in vitro differentiation of GOTO neuroblastoma cells into Schwannian cells."

* cited by examiner

*Primary Examiner* — Maureen Wallenhorst
(74) *Attorney, Agent, or Firm* — Nixon Peabody LLP; David S. Resnick; Leena H. Karttunen Contarino

(57) ABSTRACT

Described are methods for assessing recurrence status in a breast cancer patient that include assaying a biological sample from the patient for a level of a biomarker selected from such as S100β or HOX-C11, where positive detection of one or both of the biomarkers indicates a positive recurrence status. The method can be used for prognosis of poor disease free survival in a breast cancer patient, where positive detection of one or both of the biomarkers indicates poor disease survival. The method may also be used for diagnosis of recurrence, where positive detection of circulating S100β is a diagnostic variable of recurrence. The method of diagnosis is carried out on a patient who is undergoing first line therapy and/or a patient who has had surgery to remove a primary breast tumour.

3 Claims, 3 Drawing Sheets

METHOD OF ASSESSING CANCER STATUS IN A BREAST CANCER PATIENT

CROSS REFERENCE TO RELATED APPLICATIONS

This application is a 371 National Phase Entry Application of International Application No. PCT/IE2009/000015 filed Apr. 14, 2009, which designates the U.S., and which claims the benefit of priority under 35 U.S.C. §119(e) of U.S. Provisional No. 61/044,546 filed Apr. 14, 2008, and U.S. Provisional No. 61/044,549 filed Apr. 14, 2008, the contents of which are incorporated herein by reference in their entirety.

TECHNICAL FIELD

The invention relates to a method of assessing the status of a breast cancer in a breast cancer patient. In particular, the invention provides a method of predicting disease free survival and recurrence of the cancer following surgery.

BACKGROUND TO THE INVENTION

Breast cancer continues to affect one woman in ten in the western world and despite the phenomenal advances in recent years the mortality rate still remains at around 35%. Current endocrine therapies are based on manipulating the estrogen receptor (ER) by either directly targeting the estrogen receptor with ER modulators such as tamoxifen or faslodex or by reducing levels of circulating estrogen with aromatase inhibitors, such as anastrozole. Regardless of the age of the patient, adjuvant endocrine therapy, of which tamoxifen remains amongst first line, offers substantial potential benefit in terms of reduction in risk of tumour recurrence and death in women with ER positive tumours. However, while most patients initially respond to tamoxifen, in 30-40% of cases these tumours relapse within 5 years of treatment. This precipitates cessation of the regime and the initiation of second line therapy.

The development of resistance to endocrine therapy, and consequent tumour recurrence, is due at least in part to a shift in the phenotype of the tumour cell from steroid dependence to that of steroid independence/growth factor dependence. Much attention has been given in recent years to the targeting of this growth factor pathway, in particular by focusing on the growth factor receptors. Inhibitors of these receptors include herceptin, the monoclonal antibody directed against the growth factor receptor HER2, which has revolutionized the treatment of advanced breast cancer. These therapies however are effective only in a limited (25%) patient population who over-express these receptors and as such their widespread use will ultimately be limited. Despite initial favourable reports from clinical trials regarding inhibitors of both aromatase and growth factor receptors, unanswered questions remain concerning sequencing and duration of adjuvant therapy, particularly with regard to the benefit from 'priming' the tumour with tamoxifen. Furthermore due to the overriding efficacy and cost effectiveness of estrogen receptor modulators, such as tamoxifen, it is probable that these will remain important adjuvant treatments for the foreseeable future. There is therefore a pressing need to elucidate the molecular mechanisms underlying resistance to endocrine treatment and to identify patients in whom tumours are likely to recur.

STATEMENTS OF INVENTION

The invention is broadly based on the detection of proteins expressed by breast cancer tumour cells, transcription factor homeobox protein HOX-C11 (hereafter HOX-C11) and its downstream activational target S100β. Expression of each protein has been found to be strongly associated with recurrence in a breast cancer patient, especially risk of disease free survival following surgery/therapy and/or early recurrence of the cancer following surgery/therapy. S100β protein is a secreted protein which circulates in the blood, and is therefore suitable for detection in a biological fluid such as saliva or blood, thereby avoiding the need for a biopsy. The protein may however also be detected in a biopsy sample.

The invention relates to a method of assessing recurrence status in a breast cancer patient, the method comprising a step of assaying a biological sample from the patient for a level of a biomarker selected from S100β or HOX-C11, wherein positive detection of one or both of the biomarkers is indicative of a positive recurrence status.

The term "recurrence status" should be understood to mean risk of recurrence (poor disease free survival), either locally or at a distant locus, risk of metastases (and therefore recurrence at a distant locus), and/or early diagnosis of recurrence. Either biomarker may be employed as a prognostic variable of recurrence, although only circulating S100β levels may be employed as diagnostic variables of recurrence. A method of identifying recurrence is generally carried out when the patient is undergoing a first line therapy, wherein positive detection of circulating S100β levels is indicative that the tumour has recurred, and optionally that the phenotype of the cancer has "switched" from being steroid dependant to being steroid independent (growth factor dependant). Thus, in a patient who has had a primary breast tumour removed, positive detection of circulating S100β is indicative that the cancer has recurred (this will be an early indication of recurrence), and indicative that the treatment regime of the patients needs to be changed to a second line therapy (for example, a tyrosine kinase inhibitor). Thus, the term "recurrence status" may also be taken to mean determining the phenotype of the cancer, and determining an optimal therapy for the recurred cancer based on the phenotype.

The term "positive recurrence status" should be understood to mean, for example, a prognostic risk of recurrence, actual diagnosis of recurrence (for example, when the assessment is carried out after surgery and/or during first line therapy), or diagnosis of a "switch" in the cancer phenotype.

In this specification, the term "circulating S100β" should be understood as meaning S100β that is present in a biological fluid from the patient, for example blood, serum, saliva, cerebrospinal fluid, or synovial fluid; in other words, secreted S100β. Ideally, the term refers to the level of the protein in blood or a blood product such as serum.

In one embodiment, the invention provides a method of prognosis of poor disease free survival in a breast cancer patient, which method comprises detecting HOX-C11 or S100β in a biological sample from the patient, wherein positive detection of HOX-C11 or S100β is a prognostic indicator of poor disease-free survival independently of treatment. The method of detection of HOX-C11 may be performed at any time, but it would usually be performed at the time of initial diagnosis of the cancer and would generally employ tumour cells obtained in a needle punch. Alternatively, the method may be performed on tumour tissue resected during a lumpectomy or mastectomy surgical procedure. Positive detection of S100β in the biological sample from the patient predicts poor disease-free survival independently of treatment. The method may be performed at any time, but it would usually be performed after breast cancer has been diagnosed, and prior to surgery.

In another embodiment, the invention provides a method for the early detection of recurrence of a breast cancer, which method comprises detecting circulating S100β in a biological sample from the patient, wherein positive detection of S100β in the biological sample from the patient is an indicator that the cancer has recurred. Recurrence may take place locally (i.e. in breast tissue), or at a distant locus (i.e. in bone, lymph or liver). Recurrence of the cancer at a distant locus occurs when the cancer metastasizes. Thus, the method of the invention functions to detect metastasis. The predictive power of the biomarkers is sufficiently powerful to predict recurrence prior to detection using conventional methods, therefore allowing early diagnostic protocols (e.g. full body scans), early intervention and allowing informed dissensions on the commencement of second line therapies. The method of the invention may be performed at any suitable time, but it would usually be performed after the patient has undergone surgery to remove a tumour, and then periodically thereafter (i.e. every 1, 2, 3, 4, 5 or 6 months).

In another embodiment, the invention provides a method for monitoring a breast cancer therapy, which method comprises detecting HOX-C11 or S100β in a biological sample from the patient during or after the course of therapy, wherein positive detection of HOX-C11 or S100β in the biological sample from the patient indicates the presence/recurrence of the tumour. The method of the invention may be performed at any suitable time during or following a course of treatment, but it would usually be performed on a weekly or monthly basis during the treatment, and/or within one week or one month of completion of the course of treatment. Identification of the marker during the treatment would indicate that the treatment is not working optimally, and may also indicate the need for the patient to be observed and examined more closely and more regularly In another embodiment, the invention provides a method for establishing whether a breast cancer tumour has been successfully removed in surgery, which method comprises detecting circulating S100β in a biological sample from the patient following surgery. Positive detection of circulating S100β in the biological sample from the patient strongly indicates that the tumour has not been successfully removed. The method of the invention may be performed at any suitable time following surgery, but it would usually be performed within 3, 2 or 1 months, suitably within 4, 3, 2 or 1 week, of surgery to remove the tumour.

In one embodiment, the invention relates to a method of assessing the status of a breast cancer in a patient, typically a patient having an established breast cancer, comprising the steps of assessing a biological sample from the patient for S100β or HOX-C11 wherein, positive detection of S100β or HOX-C11 in the biological sample informs the metastatic potential of the tumour and predicts poor disease free survival. Ideally, the biological sample is a breast tumour specimen typically originating from surgical excision of primary neoplasm. Assessment can take place at the time of initial diagnosis, or upon recurrence.

In another embodiment, the invention provides a method of identifying breast cancer patients at risk of cancer metastases, which method comprises detecting HOX-C11 or S100β in a biological sample from the patient, wherein positive detection of HOX-C11 or S100β in the biological sample from the patient predicts tumour metastases.

The invention also relates to a method of treatment of breast cancer in a patient comprising an initial step of assessing the status of the breast cancer according to a method of the invention, and using the status obtained to design a therapy for treating the cancer. Thus, if the patient is about to undergo surgery to resect a breast tumour, and the status information obtained using the method of the invention indicates that the tumour is aggressive, and/or indicates a poor disease free survival, then a clinician may recommend a post-operative treatment regime for the cancer which is suitable for aggressive cancers. This may involve an aggressive chemotherapy or first line drug therapy, and/or more regular and robust check-ups. For example, a clinician may recommend that the patient is observed every month instead of every six months. Further, the clinician may recommend that the patient has an ultrasound or a mammogram every month. Additionally, the clinician may recommend that the patient is started on a second line therapy immediately. Likewise, if the assay of the status of the breast cancer in a post operative breast cancer patient (for example, by monitoring for circulating S100β) indicates that the cancer has recurred, then a clinician can recommend that a second line treatment is initiated immediately, and suitably also recommend more regular and robust check-ups.

Typically, the methods of the invention are suitable for patients on endocrine therapy.

In this specification, the term "biological sample" may be any sample obtained from an individual such as, for example, blood, serum, saliva, urine, cerebrospinal fluid, tissue, cells, breast cancer tumour specimen, etc. Suitably, the biological sample will be serum or breast cancer tumour specimen.

The invention also relates to a kit of parts comprising diagnostic reagents suitable for detecting in a tissue sample of biomarkers selected from the estrogen receptor (ER), optionally the HER2 receptor, and capable of positive detection of S100β or HOX-C11. Thus, the kit of parts may comprise means for detecting expression of the ER in a tissue sample, optionally, means for detection of the HER2 receptor in a tissue sample, and means for positive detection of HOX-C11 in a tissue sample and/or means for positive detection of S100β in a tissue or a blood sample. Suitably, the diagnostic reagents are suitable for immunodetection of the biomarkers. Examples of suitably diagnostic reagents are described below.

Detection of HOX-C11 may be performed according to any technique known in the art, for example by means of a tissue microarray, or immunohistochemical detection, the details of which will be well known to those skilled in the art. When employing immunohistochemical detection and the Allred Scoring system (Harvey at al 1999) [1], the term "positive detection" should be understood as meaning an Allred score of from 3 to 8. The term "positive detection" should be taken to mean a level of S100β that is greater than a reference value obtained from patients negative for breast cancer. When the biological sample is serum, "positive detection" typically means a serum level of S100β of greater than 200 pg/ml, typically when measured using the ELISA test described below. When the biological sample is a tissue sample, immunohistochemical detection and the Allred Scoring system (Harvey at al 1999) [1] may be employed to detect the protein, in which case the term "positive detection" should be understood as meaning an Allred score of from 3 to 8.

The nucleic acid and amino acid Sequences of HOX-C11 are provided in SEQUENCE ID NO's 1 and 2 and the nucleic acid and amino acid sequences of S100β are provided in SEQUENCE ID NO's 3 and 4 respectively. Given the sequences, detection of the protein may be performed by any suitable means, the details of which will be well known to those skilled in the art. In particular, the ELISA kit available froth Diasorin Ltd (Vercelli, Italy) for measuring S100β is suitable for performing the methods of the invention. Various alternative methods of detecting protein biomarkers will be apparent to the person skilled in the art. For examples, antibodies against HOX-C11 and or S100β may be raised using conventional techniques, and may be employed as diagnostic reagents in an autoantigen assay. Antibodies against HOX-C11 and or S100β may be a monoclonal or polyclonal antibody or other specific binding partner, as long as it can recognize the protein. Antibodies can be produced by using HOX-C11 and or S100β as the antigen according to a conventional antibody or antiserum preparation process. The present invention contemplates the use of both monoclonal and polyclonal antibodies in methods of detecting the presence of HOX-C11 and or S100β. Any suitable method may be used to generate the antibodies used in the methods and kits of the present invention, including but not limited to, those disclosed herein. For example, for preparation of a monoclonal antibody, protein, as such, or together with a suitable carrier or diluent is administered to an animal under conditions that permit the production of antibodies. For enhancing the antibody production capability, complete or incomplete Freund's adjuvant may be administered. Normally, the protein is administered once every 2 weeks to 6 weeks, in total, from about 2 times to about 10 times. Animals suitable for use in such methods include, but are not limited to, primates, rabbits, dogs, guinea pigs, mice, rats, sheep, goats, etc.

For preparing monoclonal antibody-producing cells, an individual animal whose antibody titer has been confirmed (e.g., a mouse) is selected, and 2 days to 5 days after the final immunization, its spleen or lymph node is harvested and antibody-producing cells contained therein are fused with myeloma cells to prepare the desired monoclonal antibody producer hybridoma. Measurement of the antibody titer in antiserum can be carried out, for example, by reacting the labeled protein, as described hereinafter and antiserum and then measuring the activity of the labeling agent bound to the antibody. The cell fusion can be carried out according to known methods [2]. As a fusion promoter, for example, polyethylene glycol (PEG) or Sendai virus (HVJ), preferably PEG is used.

Polyclonal antibodies may be prepared by any known method or modifications of these methods including obtaining antibodies from patients. For example, a complex of an immunogen and a carrier protein is prepared and an animal is immunized by the complex according to the same manner as that described with respect to the above monoclonal antibody preparation. A material containing the antibody is recovered from the immunized animal and the antibody is separated and purified.

The antibodies may be labelled with a detectable label such as, for example, a fluorescent, luminescent, or radioactive label. Typically, the antibodies will be immobilised to a support, before the support is reacted with a biological sample. The support will then be washed to remove any non-reacting proteins, before any proteins that have formed an immunospecific complex with the antibodies are identified using conventional techniques. Generally, this method is suitable for detecting the presence of S100β in biological fluid samples. When the S100β is non-circulating, in other words, when it is located in a tumor cell, the most appropriate method of detection is immunohistochemical detection. Methods of immunohistochemical detection of tumor antigens will be well known to those skilled in the art, and are described previously.

Detection may also be carried by measuring the expression of corresponding mRNA from a tumour-derived tissue or cell sample. mRNA expression may be measured by any suitable method including, but not limited to, a Northern Blot or detection by hybridisation to a oligonucleotide probe. A variety of hybridization assays using a variety of technologies for hybridization and detection are available. For example, a TaqMan assay (PE Biosystems, Foster City, Calif.; See e.g., U.S. Pat. Nos. 5,962,233 and 5,538,848,) is utilized. The assay is performed during a PCR reaction. The TaqMan assay exploits the 5'-3' exonuclease activity of the AMPLITAQ GOLD DNA polymerase. A probe consisting of an oligonucleotide with a 5'-reporter dye (e.g., a fluorescent dye) and a 3'-quencher dye is included in the PCR reaction. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence.

In other embodiments, reverse-transcriptase PCR (RT-PCR) is used to detect the expression of RNA where RNA is enzymatically converted to complementary DNA or "cDNA" using a reverse transcriptase enzyme. The cDNA is then used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S. Pat. Nos. 5,639,606, 5,643,765, and 5,876,978 is utilized.

In-vivo imaging techniques may be employed to detect the presence of HOX-C11 and or S100β. For example, HOX-C11 and or S100β, or mRNA encoding the protein, is labeled using a labeled antibody specific for the protein. A specifically bound and labeled antibody can be detected in an individual using an in vivo imaging method, including, but not limited to, radionuclide imaging, positron emission tomography, computerized axial tomography, X-ray or magnetic resonance imaging method, fluorescence detection, and chemiluminescent detection. Methods for generating antibodies to S100β are described above. In some embodiments, reagents (e.g., antibodies) specific for a specific biomarker are fluorescently labeled. The labeled antibodies are introduced into a subject (e.g., orally or parenterally). Fluorescently labeled antibodies are detected using any suitable method (e.g., using the apparatus described in U.S. Pat. No. 6,198,107). In other embodiments, antibodies are radioactively labeled. The use of antibodies for in-vivo diagnosis is well known in the art. Sumerdon et al [3] have described an optimized antibody-chelator for the radioimmunoscintographic imaging of tumors using Indium-111 as the label. Griffin et al, [4] have described the use of this agent in detecting tumors in patients suspected of having recurrent colorectal cancer. The use of similar agents with paramagnetic ions as labels for magnetic resonance imaging is known in the art [5]. The label used will depend on the imaging modality chosen. Radioactive labels such as Indium-111, Technetium-99m, or Iodine-131 can be used for planar scans or single photon emission computed tomography (SPECT). Positron emitting labels such as Fluorine-19 can also be used for positron emission tomography (PET).

DETAILED DESCRIPTION OF THE INVENTION

The genomic actions of estrogen are mediated through its nuclear receptor, leading to the transcription and translation of genes relevant to tumour progression. The ER is encoded for by 2 genes, ER-α and ER-β. The magnitude of ER gene regulation is influenced, not only by the ligand, but also by the presence of specific co-regulatory proteins, present at rate limiting levels, which modulate transcription. Over the past few years a number of nuclear receptor interacting proteins have been identified including the p160 family coactivator proteins—steroid receptor coactivator-1 (SRC-1/NCoA-1), SRC-2 (TIF2/GRIP1) and SRC-3 (AIB1/pCIP/RAC3/ACTR). The SRC coactivator proteins can enhance nuclear receptor transcriptional activity by enabling access of transcription factors and RNA polymerase II core machinery to target DNA. Despite the well documented redundancy between members of the SRC family, it is clear from functional studies that individual SRCs harbour the capacity to regulate distinct biological processes.

The transcriptional coactivator SRC-1 is a strong predictor of reduced disease-free survival in breast cancer patients on endocrine treatment, outperforming all standard predictors as well as a variety of other breast cancer related proteins. At a cellular level the development of endocrine resistance is associated with a shift towards a growth factor dependent phenotype. SRC-1 can utilise non-steroidal transcription factors to mediate its activity. Proteomic, molecular and translational investigations have revealed HOX-C11 as a functional transcription factor host for SRC-1.

Without being bound by theory, it is postulated that SRC-1 interacts with the non-steroidal receptor transcription factor HOX-C11 to activate target genes and drive the steroid-independent phenotype of the resistant breast cancer cell. HOX proteins are members of the homeodomain transcription factors which are involved in a host of cellular functions including organogenesis, cellular differentiation, migration, cell cycle and apoptosis. Differential expression of HOX-C11 is associated with several cancers including those of the colon, cervix, prostate and breast.

Figure 1:
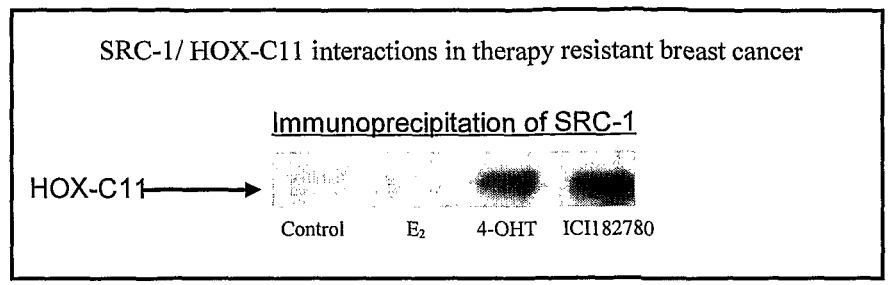
FIG. 1: Confirmation of differential interactions between SRC-1 and HOX-C11 in endocrine resistant breast cancer LY2 cells in the presence of tamoxifen (4-OHT) and faslodex (ICI) ($10^{-8}$ M) was performed by immunoprecipitation of SRC-1 and subsequent immunoblot for HOX-C11.
Figure 2:
FIG. 2: Immunohistochemical localisation of HOX-C11 in breast cancer tissue.
Figure 4A:
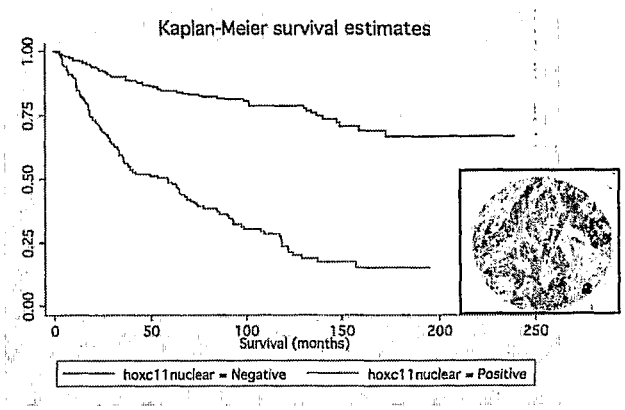
FIG. 4A—Kaplan Meir estimates of disease-free survival in primary breast cancer patients treated with tamoxifen according to HOX-C11 (N=560)
Figure 4B:
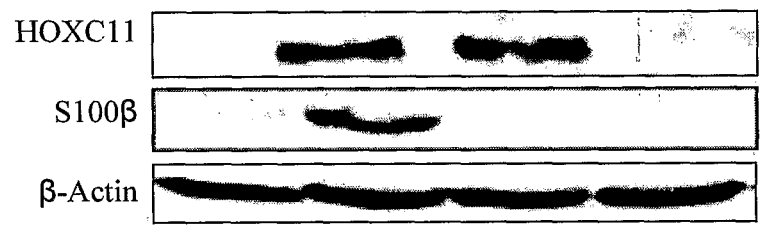
FIG. 4B—Overexpression of HOXC11 in endocrine resistant LY2 cells up-regulated protein expression of the putative target gene S100β in comparison to control. Knock down of SRC-1 inhibited the HOXC11 induced up-regulation of S100β.
Figure 4C:
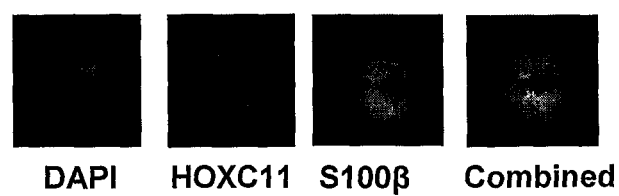
FIG. 4C—Co-localisation of HOXC11 and S100β in breast cancer tissue.

Increased interactions between HOX-C11 and SRC-1 were found in endocrine resistant versus endocrine sensitive breast cancer. Furthermore these interactions were enhanced in the presence of endocrine modulators, tamoxifen and faslodex (FIG. 1). In primary breast cancer tissue HOX-C11 and SRC-1 were co-localised to the nucleus and perinuclear region of the tumour epithelial cells (FIG. 2). A greater interaction occurred in tamoxifen-resistant LY2 cells, compared with the parent MCF-7 sensitive cell line. HOX genes play a central role in ductal formation and lobulo-aleolar development by regulating epithelial proliferation and differentiation in the developing breast and have been implicated in steroid/growth-factor pathway crosstalk. Moreover HOX-C11 was found to be a strong predictor of disease-free survival on endocrine treatment (Hazard ratio: 5.79; p<0.0001) (FIG. 4A). HOX-C11 was confirmed to be over expressed in tamoxifen-resistant cells using immunocytochemistry and was observed to translocate to the nucleus and peri-nuclear region when cells were treated with tamoxifen and faslodex. S100β has been identified as a possible target gene of the HOX-C11 transcription factor. Several HOX responsive elements have been identified in the promoter of S100β and forced expression of HOX-C11 in neuronal cells induces expression of S100β. This family of calcium binding protein is secreted and has previously been associated with poor outcome and reduced disease-free survival in melanoma. Experimental data provides evidence for a functional interaction between SRC-1 and HOX-C11. Knockdown of SRC-1 using siRNA abrogated the HOX-C11 associated induction of S100β (FIG. 4B). Furthermore, using immunohistochemical techniques S100β was co-localised with HOX-C11 to the tumour epithelial cells in breast cancer tissue (FIG. 4C). These data establish S100β as a target gene of HOX-C11/SRC-1 interactions.

HOX-C11 protein expression and that of its target gene S100-β was examined in a large cohort of breast cancer patients (n=560). Kaplan Meier estimates of disease-free survival indicate strong associations between HOX-C11/S100-β and reduced disease-free survival in patients. We conducted a $\chi^2$ analysis of HOX-C11 and S100β expression and time to recurrence, nodal status and metastasis (local and distant) (See Table 1 below). Significant associations were noted between HOX-C11 and S100β expression and recurrence and metastasis at both local and distant sites. We applied a Cox proportional hazards model and found HOX-C11 to be a strong predictor of disease recurrence (hazard ratio: 5.79). These findings indicate that HOX-C11 is a better predictor of disease-free survival than any of the standard clinicopathological parameters currently in use.

TABLE 1

Associations between HOXC11 and S100β expression and clinicopathological parameters in breast cancer tissue

|  | HOXC11 p-value | S100beta p-value |
|---|---|---|
| Cs Nodal Status | 0.4037 | 0.216 |
| Cs Local | <0.001* | <0.001* |
| Cs Distant | <0.001* | <0.001* |
| Cs Recurrence | <0.001* | <0.001* |

Figure 5A:
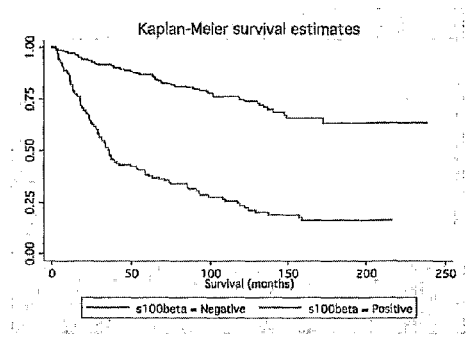
FIG. 5A—Kaplan Meir estimates of disease free survival in primary breast cancer patients treated with tamoxifen (N=560). Disease free survival according to S100β.

The Cox proportional hazards model also found S100β to be a strong predictor of disease recurrence (hazard ratio: 5.829625) (FIG. 5A).

Figure 5B:
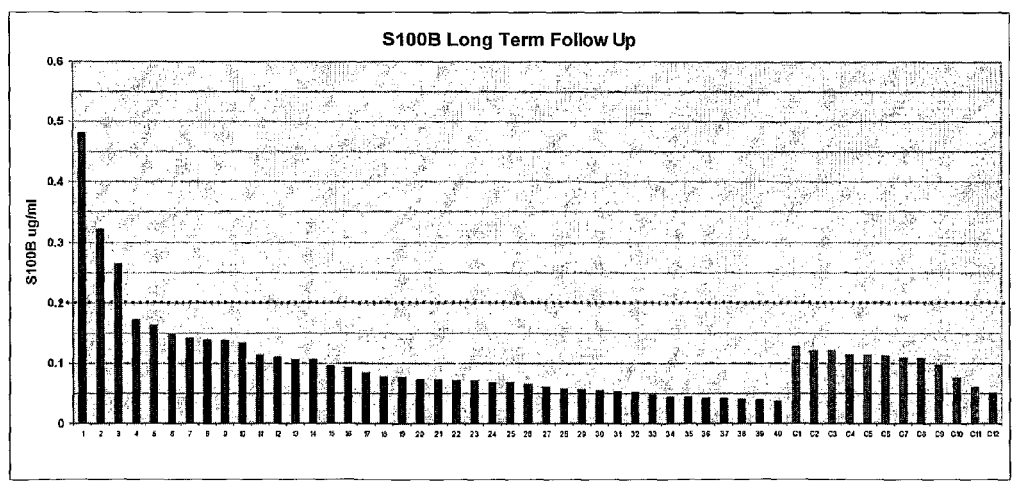
FIG. 5B—Pre-operative S100β protein levels in breast cancer patients (n=40) and aged matched controls (n=12).

S100β levels were measured in blood samples from breast cancer patients (n=40) and aged matched controls (n=12). Pre-operative breast cancer patient serum levels of S100β were found to be 30 times that of matched normal controls (FIG. 5B). Furthermore elevated levels of S100beta were found to strongly associate with disease recurrence (p=0.002), (Table 2). These data indicate S100β as a robust serum marker of tumor progression in breast cancer patients.

TABLE 2

Associations between S100β expression in breast cancer
patient bloods and clinicopathological parameters

|  | p-value |
| --- | --- |
| Cs Nodal Status | 1 |
| Cs Local | =0.224 |
| Cs Distant | =0.004* |
| Cs Recurrence | =0.002* |

Tissue Microarray HOX-C11

Figure 3:
FIG. 3: Tissue microarray HOX-C11.

HOX-C11 protein can be detected within paraffin-embedded breast tumour specimens originating from surgical excision of primary neoplasm. Slides from paraffin-embedded tumour are reviewed for representative areas of tumour and tissue arrays can then be prepared. For example three 0.6 mm punches could be taken from the selected areas in each block and then be mounted in a recipient block containing 150-300 biopsies (FIG. 3). Biopsies from normal breast tissue should be included as controls.

Slides are then evaluated using light microscopy. They can also be assessed using the Ariol SL-50, utilising special systems for the detection and quantification of membranous, cytoplasmic and nuclear stains.

A map of the cores on the tissue microarray are replicated on a computer file, which is used to identify each individual patient.

Immunohistochemical Assessment of HOX-C11 Expression.

Immunohistochemistry is the localization of antigens in tissue sections by the use of labelled antibodies as specific reagents through antigen-antibody interactions that are visualized by a marker such as an enzyme or a fluorescent label. An unlabelled primary antibody is incubated on the tissue section, binding the antigen of interest. A biotinylated secondary antibody directed against the primary antibody is then applied. A strepavidin-biotin complex (ABC) which possesses biotin binding sites is then added, cross reacts with the biotin molecules on the secondary antibody, amplifying the signal intensity.

Four micron thick tissue sections were cut from paraffin embedded breast tumour tissue blocks and mounted on SuperFrost Plus slides (BDH, Poole, UK). Sections were dewaxed by passage through xylene (×2)(BDH) for 5 minutes each and rehydrated by immersion in alcohol of decreasing Concentrations (2×100%, 70%) for 5 minutes in each container. The sections were then washed in tap water (5 minutes) and in distilled water (5 minutes). Endogenous peroxidase activity was blocked using 3% hydrogen peroxide (Sigma-Aldrich, Steinheim Germany) in distilled water (20 minutes). Slides were then washed in tap water and in distilled water for 5 minutes each. Antigen retrieval was performed by immersing sections in 0.01 M sodium citrate buffer pH 6 (Sigma-Aldrich) and microwaving on high power for 7 minutes and then 15 minutes on medium/low. Sections were then left to cool to room temperature (approximately 30 minutes). A liquid-repellant pap pen (Daido, Sangyo, Tokyo Japan) was used to mark out the tissue on the slides. Sections were blocked in goat and rabbit serum (Vector Laboratories, Burlingame Calif. USA) for 60 minutes in room temperature. Sections were incubated with primary antibody; chicken anti-human HOX-C11 polyklonal IgY (1 mg/ml) (GenWay Biotech, San Diego, Calif. USA) (1:25) for 60 minutes at room temperature. Sections were then washed in PBS (5 minutes). They were subsequently incubated with the corresponding biotin-labelled secondary antibody; goat-anti-chicken IgY (GenWay Biotech) (1:500) in PBS for 60 minutes. Sections were washed in PBS (5 minutes). Peroxidase-labelled avidin-biotin complex (Vector Laboratories, Burlingame Calif. USA) were added to the biotin-labelled antibody for 30 minutes and then washed in PBS (5 minutes). Sections were developed in 3,3-diaminobenzidine tetrahydrochloride (FastDAB, Sigma-Aldrich) for 7 minutes, then washed in distilled water (5 minutes). Sections were then counterstained with Mayer's Hematoxylin Solution (Sigma-Aldrich) for 2 minutes and then washed in PBS (5 minutes). Negative controls were performed using matched IgG controls (Santa Cruz Biotechnology, California USA) and omission of the primary antibody. Sections were then passed through increasing concentrations of alcohol (70%, 2×100%) and then xylene (×2). Cover slips (BDH) were applied to the sections with DPX mountant (BDH).

Each entire slide was evaluated by light microscopy using the Allred System described in Harvey et al. [5]. First, a proportion score was assigned, which represented the estimated proportion of tumor cells positive for nuclear HOX-C11 (0, none; 1, <1/100; 2, 1/100 to 1/10; 3, 1/10 to 1/3; 4, 1/3 to 2/3; and 5, >2/3). Next, an intensity score was assigned which represented the average intensity of nuclear HOX-C11 protein expression in positive tumor cells (0, none; 1, weak, 2, intermediate; and 3, strong). The proportion and intensity scores were then added to obtain a total score, which ranged from 0 to 8.

Clinical-Pathological Parameters HOX-C11

Breast cancer patients are diagnosed by core biopsy or FNAC (Fine needle aspiration cytology). Patients are treated with neoadjuvant hormonal therapy and chemotherapy prior to surgery.

All patients are assessed by abdominal ultrasound, chest X-ray and bone scintigraphy before surgery. HER2 status was evaluated using the DAKO HercepTest immunocytochemical assay (Glostrup, Denmark). Variables analysed include tumor size, tumor grade, tumor stage, estrogen receptor status, Her-2/neu receptor status. Histological grading is performed by a pathologist using the Eliston-modified Scarff-Bloom-Richardson system. All patients in the preliminary study underwent total or segmental mastectomy with level I, II and III axillary dissection. Time to disease progression was defined as the period from the initiation of treatment to the time of disease recurrence or death.

Statistical Analysis HOX-C11

SAS version 8.2 statistical program (SAS Institute, Cary, N.C., USA) was used in the statistical analysis. Univariate analysis was performed using Fisher's exact test for categorical variables and Wilcoxon's test for continuous variables. Multivariate analysis was carried out using Cox's proportional hazard model. A p-value of less than 0.05 was considered to be significant. Survival times between groups were compared using the Wilcoxon test adjusted for censored values.

Detection of Human S-100β ELISA Kit

This ELISA kit Diasorin Ltd (Vercelli, Italy) is used for quantitative determination of human S-100β in plasma sample.

Test Principle

The Sangtec® 100 ELISA is a two-site, one-step, enzyme linked immunosorbent assay. In the assay calibrators, controls and unknown samples react simultaneously with 2 solid phase capture antibodies and a detector antibody conjugated with horseradish peroxidase (HRP) during the incubation in the microtiter wells. After a washing step a TMB chromogen is added and the reaction is allowed to proceed for 15 minutes. The enzyme reaction is stopped by adding a Stop Solution and the absorbance is measured at 450 nm.

Kit Contents
  HRP—conjugate: Contains a monoclonal mouse anti-S-100B antibody conjugated with HRP, BSA and 0.5% ProClin 300 as preservative.
  Calibrators: 2 vials of each of 6 calibrators. Reconstitute in 1.0 mL purified water. Calibrators consist of S-100 bovine antigen. Calibrator S-100 value is listed on the vial labels.
  Controls: 2 vials of each 2 controls, Reconstitute in 1.0 mL purified water. Controls consist of S-100 bovine antigen.
  Wash Buffer 10×: a PBS-Tween concentrate.
  TMB Solution: Buffered substrate and chromogen, colorless, 0.05% TMB (3,3', 5,5' Tetramethylbenzidine). Protect from light.
  Stop Solution: Contains 0.4N Sulfuric Acid.
Method
Preparation of Calibrators and Controls
  Allow unopened reagents and samples to reach room temperature (20-25° C.) before use.
  Calibrators: Reconstitute in 1.0 mL purified water. Let stand 20 minutes. Mix carefully.
  Controls: Reconstitute in 1.0 mL purified water. Let stand 20 minutes. Mix carefully.
  10× Wash Buffer: Dilute 1:10 (1× Wash Buffer) with purified water.
Procedure
  Prepare all the reagents as described. Mix the samples before pipetting.
  Pipette 50 µL of calibrators, controls and unknown samples into the wells.
  Add 150 µL conjugate to all wells.
  Cover the plate and incubate for 2 hours on a plate shaker (800 rpm) at room temperature (RT).
  Wash 3 times with 300 µL of 1× Wash Buffer.
  Add 100 µL TMB substrate to all wells.
  Cover the plate and incubate 15±2 minutes on a plate shaker (800 rpm) at room temperature.
  Stop the reaction by adding 100 µL Stop Solution. Add the Stop Solution in the same order and speed, which was used for the TMB substrate.
  Read the absorbance at 450 nm using a microplate reader within 15 minutes.
  The Cubic Spline algorithm should be used for calculation of results.
Performance Characteristics
  Reference Range: Cut-off was determined to 0.20 µg/L (the 95%-ile of 100 blood donor samples).
  Measuring Range: The measuring range is up to 5 µg/L. Concentrations for high samples can be obtained by diluting with Sangtec® 100 ELISA Diluent and repeating the assay.
  Precision: Serum samples at different concentration levels were evaluated running one assay per day over ten operating days. Intra-assay and Inter-Assay precision was estimated by analysis of variance (ANOVA). Within the range of concentrations from 0.18 to 4 µg/L, the within run imprecision is <10% and the total imprecision is <15%.
  Sensitivity: The detection limit is 0.03 µg/L.

Immunohistochemical Assessment of S100β Expression.

Immunohistochemistry is the localization of antigens in tissue sections by the use of labelled antibodies as specific reagents through antigen-antibody interactions that are visualized by a marker such as an enzyme or a fluorescent label. An unlabelled primary antibody is incubated on the tissue section, binding the antigen of interest. A biotinylated secondary antibody directed against the primary antibody is then applied. A strepavidin-biotin complex (ABC) which possesses biotin binding sites is then added, cross reacts with the biotin molecules on the secondary antibody, amplifying the signal intensity.

A slide comprising the tissue section is evaluated by light microscopy using the Allred System described in Harvey et al. [5]. First, a proportion score was assigned, which represented the estimated proportion of tumour cells staining positive for S100β (0, none; 1, <1/100; 2, 1/100 to 1/10; 3, 1/10 to 1/3; 4, 1/3 to 2/3; and 5, >2/3). Next, an intensity score was assigned which represented the average intensity of positive tumour cells (0, none; 1, weak, 2, intermediate; and 3, strong). The proportion and intensity scores were then added to obtain a total score, which ranged from 0 to 8. A score of 3 or greater represents a positive detection within the meaning of the assays of the invention.

The invention is not limited to the embodiments hereinbefore described which may be varied in construction and detail without departing from the spirit of the invention.

References
1. Harvey et al. Journal of Clinical Oncology, 17, 1474[1999]
2. Koehler and Milstein (Nature 256:495 [1975])
3. Sumerdon at al, (Nucl. Med. Biol 17:247-254 [1990]
5. Griffin et al, (J Clin One 9:631-640 [1991])
5. Lauffer, Magnetic Resonance in Medicine 22:339-342 [1991])

The invention claimed is:

1. A method for treating breast cancer in a breast cancer patient identified as having a positive recurrence status comprising a step of treating the patient with a second line therapy comprising a step of
   (a) identifying the breast cancer patient having positive recurrence status by assaying a biological sample from the patient for a level of a biomarker selected from S100β or HOXC11, wherein positive detection of one or both of the markers is indicative of a positive recurrence status, wherein when the biomarker is HOXC11 positive detection means an Allred score from 3-8 for nuclear HOXC11, and when the biomarker is S100β positive detection means a level of serum S100β greater than 200pg/ml or an Allred score from 3-8 for tumor cells, and
   (b) administering to the breast cancer patient having a positive recurrence status a second line of therapy.

2. The method of claim 1, wherein the positive recurrence status indicates one or more of risk of poor disease survival, risk of recurrence, risk of metastasis, and diagnosis of recurrence.

3. The method of claim 1, wherein the second line therapy comprises administering to the breast cancer patient a tyrosine kinase inhibitor.

* * * * *

UNITED STATES PATENT AND TRADEMARK OFFICE
CERTIFICATE OF CORRECTION

PATENT NO. : 8,501,483 B2 Page 1 of 1
APPLICATION NO. : 12/937439
DATED : August 6, 2013
INVENTOR(S) : Young et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 38 days.

Signed and Sealed this
Fifteenth Day of September, 2015

Michelle K. Lee
*Director of the United States Patent and Trademark Office*

SEQUENCE LISTING

```
<160> NUMBER OF SEQ ID NOS: 4

<210> SEQ ID NO 1
<211> LENGTH: 3294
<212> TYPE: DNA
<213> ORGANISM: Homo sapiens

<400> SEQUENCE: 1
gtgctcagag agagagagac taagacggat aacgcgtcat ctcgccttcc caaattttcc      60
cccctcgcta gaccgggtcc aaaacctcca tccggagccg gcaggagagg agaacgatgt     120
ttaactcggt caacctgggc aacttctgct ctccgtcgcg caaggagagg ggcgcagatt     180
tcggcgagcg agggagctgc gcctccaacc tctatctgcc cagttgcact tactacatgc     240
```

```
ccgagttctc cacggtctcc tccttcctgc cccaggcccc ctctcgtcag atctcctatc    300
cctactcggc ccaagtgccc ccggtccggg aggtctccta cggcctggag ccatccggca    360
agtggcacca tcggaacagc tactcctcct gctatgcggc ggccgacgag cttatgcacc    420
gggagtgcct gcctccttcc accgtcaccg agatcctcat gaaaaacgaa ggctcctacg    480
gcggccacca ccaccccagc gccccgcacg caaccccccgc cggcttctac tcctcagtca    540
acaagaacag cgtcctgcct caagccttcg accgtttctt cgacaacgcc tactgcggtg    600
gcggcgaccc gcccgccgag cccccctgct ccggcaaggg cgaggccaag ggggagcccg    660
aggcaccccc ggcctcggga ctggcgtccc gggctgaggc gggtgccgag gcggaggctg    720
aggaggagaa cacaaatccc agctcgtccg gttcagccca ctccgtggcc aaggagccgg    780
ccaaaggagc cgcccccagt aggtagcagc ggccggggaa cgggcgggca gcgagggagg    840
gagcgagaga gggagggcga gagaaggggg gaggcaaggg gagcggggac ggcctcgtgt    900
tttgggtcag tccgatttta tgtggagttt tataagcatt caaaggattt tattataacc    960
tacaaagccc tctctcccaa cgactcgact ttttacgatg gagaaggggt ggggagggag   1020
ggaaaagggc tctttggaaa agccgggtga accccctcc cccgttatct ccctcggtct   1080
gtgaaatttt taaaagcgca accattgcgg gcgatattaa ctttgatcgt gaacttagag   1140
gagcatttaa ggaagtatgg ggagccgggc tgccgaggag tggggaggag gggaggggtg   1200 gaggggggaga aaggggaggg cgagggaaag acagggagag atccagagag ggggagaggt   1260 ggggagagg agcaatggag cagaacctga gaccggagag gcaagccagg accgctatga   1320
tccttcttaa aactagttttt gaaaatgttc aaactatgtg ttcgcgggtc ctcgagcaga   1380
aacccaagca actctggggt cagcggcgac aggggaatgg ggcgaggcgg cgcaggactc   1440
cactgcgttc caggcggggg tctgggcgtt tctccccggt ccgcggcctt agtgcttgcc   1500
tagaactgcg gtgtggaagg cgctgccccg cgggcttccc ggggcgccag gccccggaa    1560 gcggctctct ggtgtctcgg tgcctgctgg ccggcttcct ccccgcctcc cgactgctct   1620
cgccagattt cactgcttcg cgcctgttct cagcttt ccc ccagatttc tgggggaggg   1680 gttgggcttt ccgaaccact aggagggcgg cccaggaagg gcccgagggc ggaggggag    1740 cagacagggg gcccgagggg acgcacgtgt acctggaggg cttccttct gtcccagacc   1800 ctgtcagccg cggctctcgc ctgagaactg ggacgggggt ggcgcagtgg cggggggtg    1860 gggacccgct agacctggca ggggtcgag gcttgccggg gtgctgcggc tgcaggagag   1920
ccagccgcct ggcggaggg ctgccgcgcg tgggctagga aagggccgc tgagcgctca    1980 gcgggctggg gtcgcccggg tctcacgtgt ctctctcccc cctctcctcg cacttgcccc   2040
ctcccctccc tccagacgcc ccccgcaccc gcaagaagcg ctgcccttat tcgaaattcc   2100
agatccggga actggagcga gagttttttct tcaacgtgta tatcaacaaa gagaagcggc   2160
tgcagctgtc ccggatgctg aacctgacgg accgacaagt gaaaatttgg tttcagaaca   2220
gaaggatgaa agaaaagaaa ctgagcagag accggctgca gtatttctcg ggaaatcctc   2280
tgctgtaacc tgcagaccgg gcccttttgg gggcgggggg aggggaaaat tattttattt   2340
tatttttatt ttttattttc taactcgtct tctttccgcc ggtggaaaac tggactgtgg   2400
ccagggctgg cccccaccgc tgtggccggc actccattcc ggaacctcct ggaccctcta   2460
tctgactctc gctgtgggac agggaccggg cctggaaagg gggtgaaggg aagtgtctga   2520
tgcacggcga gtgaacaccg ttggcgccga ggccaagact ttgatttaaa agaaaacaca   2580
cctcggcgac aatgtcttgc tgctcggatt aggtggggga ggggcgacag tagtgagcgc   2640
```

-continued

```
ctgagccgaa caatcctcga actaaaagcc ttcccttgcc catgtgaaaa gatccgctaa    2700
gacagcatgt ctgccagcgg aaacttctcg agctccccc  tctacccgc  cccaccttgc    2760 agctaaatgt gatcctgcct tgctgtgaaa tttctgtacc ttcaacctgg tgttaggtgt    2820
gcaaagtccg tgtcctacct ccgtcttcgc caaggccccg cccgagccta gttgttctcc    2880
ccctgaatgt gtagaacctt cctttgaaat tcttaatcg  gtgcattgag gtttccacat    2940 cttttttccaa gcagtgcccc acttcatgga tttatagcta tagtctatgc agtcgttacc    3000
tctttttttt tttttttttaa gaaaattgaa gattggggtg gtggaggcag tagggagatg    3060
ggattgggca cctcccccgt gctggggcct ggattttgt  aaataaattt cccaagcgtt    3120
tctttccacc tggagggaaa ggggggacg  ccccagtga  gattcaaatc acgcatctct    3180
actcctctgc gtgagtgcgt gtgtacatgt gcactcccca ccctgctccc ttcccagagg    3240
gattgctgtg aaattttttt ggtggcaaat aaagataaat ttcattctgt tcaa           3294
```

<210> SEQ ID NO 2
<211> LENGTH: 304
<212> TYPE: PRT
<213> ORGANISM: Homo sapiens

<400> SEQUENCE: 2

```
Met Phe Asn Ser Val Asn Leu Gly Asn Phe Cys Ser Pro Ser Arg Lys
1               5                   10                  15

Glu Arg Gly Ala Asp Phe Gly Glu Arg Gly Ser Cys Ala Ser Asn Leu
            20                  25                  30

Tyr Leu Pro Ser Cys Thr Tyr Tyr Met Pro Glu Phe Ser Thr Val Ser
        35                  40                  45

Ser Phe Leu Pro Gln Ala Pro Ser Arg Gln Ile Ser Tyr Pro Tyr Ser
    50                  55                  60

Ala Gln Val Pro Pro Val Arg Glu Val Ser Tyr Gly Leu Glu Pro Ser
65                  70                  75                  80

Gly Lys Trp His His Arg Asn Ser Tyr Ser Ser Cys Tyr Ala Ala Ala
                85                  90                  95

Asp Glu Leu Met His Arg Glu Cys Leu Pro Pro Ser Thr Val Thr Glu
            100                 105                 110

Ile Leu Met Lys Asn Glu Gly Ser Tyr Gly Gly His His Pro Ser
        115                 120                 125

Ala Pro His Ala Thr Pro Ala Gly Phe Tyr Ser Ser Val Asn Lys Asn
    130                 135                 140

Ser Val Leu Pro Gln Ala Phe Asp Arg Phe Phe Asp Asn Ala Tyr Cys
145                 150                 155                 160

Gly Gly Gly Asp Pro Pro Ala Glu Pro Pro Cys Ser Gly Lys Gly Glu
                165                 170                 175

Ala Lys Gly Glu Pro Glu Ala Pro Ala Ser Gly Leu Ala Ser Arg
            180                 185                 190

Ala Glu Ala Gly Ala Glu Ala Glu Glu Glu Asn Thr Asn Pro
        195                 200                 205

Ser Ser Ser Gly Ser Ala His Ser Val Ala Lys Glu Pro Ala Lys Gly
    210                 215                 220

Ala Ala Pro Asn Ala Pro Arg Thr Arg Lys Lys Arg Cys Pro Tyr Ser
225                 230                 235                 240

Lys Phe Gln Ile Arg Glu Leu Glu Arg Glu Phe Phe Asn Val Tyr
                245                 250                 255

Ile Asn Lys Glu Lys Arg Leu Gln Leu Ser Arg Met Leu Asn Leu Thr
            260                 265                 270
```

Asp Arg Gln Val Lys Ile Trp Phe Gln Asn Arg Arg Met Lys Glu Lys
        275                 280                 285

Lys Leu Ser Arg Asp Arg Leu Gln Tyr Phe Ser Gly Asn Pro Leu Leu
        290                 295                 300

<210> SEQ ID NO 3
<211> LENGTH: 6466
<212> TYPE: DNA
<213> ORGANISM: Homo sapiens

<400> SEQUENCE: 3

| | | | | | |
|---|---|---|---|---|---|
| tgccgcccag | gacccgcagc | agagacgacg | cctgcagcaa | ggagaccagg | aagggggtgag | 60 |
| acaaggaaga | ggtgagaaag | agccaggcca | agaggacgct | caggaagaaa | tggttctttt | 120 |
| cttttgggtg | gaacggaatg | gagggggtaga | aactaagtgg | tagcttaaaa | agccccttta | 180 |
| ggacaattgg | cagcatttca | gaagtgtcaa | taggatgatg | tgttttaatc | tccacattac | 240 |
| tgctgctttg | tggacacctg | actgcatcag | ccctagacag | ctagaggtgt | gtttttgccat | 300 |
| aaatcagaga | aacgtcaggt | ttcatggccc | agaagtgatt | gttgacattt | tcccagcggt | 360 |
| actacaaata | ctgcctcttc | tgtaactatt | tgaagagtaa | agattttgct | tcccactggg | 420 |
| gctaaaaatg | atggagaacc | taatgctagt | ttagtcctat | atcataaata | aatgcttccc | 480 |
| ttttctcctt | atatttcttc | caccgccctg | ggtaagtaac | tcttcagttt | tccagtttcc | 540 |
| ctcagtttga | agtgccaggg | tccccacagc | cccaggacgc | cactcagaaa | ttacgtaaca | 600 |
| attacaaata | aattgggtca | agaaatcgg | ggttttggtg | ggttttaact | ttcctcagtc | 660 |
| tcacagtttc | tcagggaggt | cgaacccctt | ctttagaggg | atcctcacac | gctaggtaac | 720 |
| ttgtctttct | aaggagttaa | agttcaaaag | ttctcttgtt | ctcaatatta | aaagattaat | 780 |
| gtaggacatt | caaagaatgt | gagaaagaaa | cggacattta | tttccatttc | tcttaaaaga | 840 |
| taaactataa | accatcaact | atttcttagg | tcaaagggaa | aaatttaaca | agaatttaat | 900 |
| tgatttgtag | tgtggttatg | aagaaaacca | tattttctag | tggtttctat | tagtgttcta | 960 |
| atatatggga | tacatgtttt | atgcctttcc | tttgtaataa | tcccattagt | cacaattcat | 1020 |
| agaaaaacaa | tttaacctcc | ttttccccaa | atcatcatgg | actttgagga | gcatcagaat | 1080 |
| gatgtaaaag | tgtcttgttt | tgtttaaaaa | aatacacaca | catacaaaca | tgcatatatc | 1140 |
| aataattgaa | aacttgagtg | caaagaataa | gaaagcatga | aatgttaaag | attttaatcc | 1200 |
| atcttaattg | ttctatttgt | gaattatcaa | attttaggg | actcaagagc | aaaataaagt | 1260 |
| acactgatta | ttaatagaat | gactttagca | aagatctggc | cagtataaaa | aaatcttcaa | 1320 |
| tcctgttttcc | ttcggaggat | cagaaataaa | taaaataatt | ccaaattatt | tttaagatgt | 1380 |
| aagttatata | ttcaacatgg | gaatgatttt | tcaacactat | ttgatttatt | aatttgtttt | 1440 |
| taattatgac | agcgcaaacg | ttcttatta | atgattagaa | ctcaaggcca | aaagctggta | 1500 |
| aatttctctg | actgcgcatc | tgttttgtga | aacaactgac | aaggcaacct | ttgtaaaatg | 1560 |
| cgcctcattc | ccagactgac | cagatatttc | cttggttcgt | aggctgtggc | gtaaggtact | 1620 |
| tgctgtgagg | gaggtagggg | ggctcttact | ttgacagctg | cagagaaaca | cctattcctg | 1680 |
| cccccacccc | ctcccgccgt | cccagtcact | gcagtgaatg | agccacccctt | tcggtacact | 1740 |
| ggaggtggaa | tgcaggctca | gcagctcagc | ttttgctgg | attctgtccc | tccctgcgac | 1800 |
| agaaccacac | ccatttgatc | agttaaactt | aggatacatt | tttttttcct | ggtagatcaa | 1860 |
| ataactttca | ctgttattct | tcaaaaagat | tgcggcaatt | ctaccatatt | tatttttcct | 1920 |
| gatgaatttt | acagctgttt | ttgtcatgtc | acccatccaa | aaaaattcca | ttgttttat | 1980 |

```
taaaaatgat ttaaatttac atatgaattt aaaggaaaaa cttcctacat tttatgttcc    2040
tcagaatctc ttggaaggac ctacgttttt cttcctaaac ttagtcttag atcacatgtt    2100
attgctatat gcataggata ttttgcactg tattttctac ttctttactg atagaatata    2160
ggaatgctat tgattttttg tcttcttatt ttgctcctag tcactgtctc actttcagat    2220
tgattttaac agcttgcagt tgatggtttg ctcacctgca ctctaccacc tcatcttgga    2280
gccttgcagg aacagagagg gaccctgtgg ggattaattc aggggaaatt aatccctgaa    2340
ttcccttgct gctctgcctc tgtattttg ccagtttccc tgttggccca acccagccag     2400
aattcagagg gcatgggaat atatccccgt ggcccacacg gacagagaag gcaggcccac    2460
agctgtctaa gaggccggtg gaaggattat gataaaagtg caaattccca gaatgcccct    2520
ccaggccatg cctgctgctc tgagcttgaa aagagtgcca aggccattcc atccccttg     2580
tctgggttga ggtctgtatt gataacatat gaaatgtttt aggatgaggt atagatgaga    2640
aggcaacttt cctttgcgag cccctaggat gtctgagctg gagaaggcca tggtggccct    2700
catcgacgtt ttccaccaat attctggaag ggagggagac aagcacaagc tgaagaaatc    2760
cgaactgaag gagctcatca acaatgagct ttcccatttc ttagaggtga gtcttgcttt    2820
ttaaacttga cactttctcc atctcctctt aaaatccatc tgtacactgg ctttatcttc    2880
tcagctgccc tgaaggtgat ttcatttccc ttccaagact cctgggctgc ttctgcaaac    2940
ttgtttgagt aacggaaccc tcagtgtggg gctggctcaa atgagcccct tgttttcatt    3000
tccttatcaa ccatcttgtg tacagtaggg gcatcaaggt cccaaaggcc aaagcgtccc    3060
aaataatgct agactcatta cttaccatgg accaaaggga acataaaagg aaactgttaa    3120
aaataagctt tgggaatgtt tttaggaaaa ggatatattt tggctttagc tagaagttta    3180
gtatttgcta tggagataag atatgccaga cttttcactca gtaaacactg actgagcact    3240
aattaagaac tgtgagatat gcaggcacga cagacatggc ttctgctctg ggcacccag     3300
cctggcacat ggatgaatga ccatgactgg cttaactgag gacgtgacag gggtctgtac    3360
acatcctttg gaagccctgg ggcttttgcag gaggctctgt ggagtaacgg atattggtga   3420
ggaactgtct ttagttgggg cccctacttt aggaagctgt gtggggggctc ctggcaagcc   3480
ctgttcttca ggcagttccc gctgtggctt gtggtggaag tatgtccaga cccttgcatt    3540
agggctcatt ttcctaccca ccgtctccac tgtccttgga tcagacccac ctgtctttac    3600
tgcccacctc atgccctcat ggaagtgaac tgtgatcccc ctggtacctg atgctctctt    3660
agaaccaagg ctggcttgag gcacgccttg agccagagtg aagcaccagt ggtgtgcaca    3720
tatgaaacgt agtgaagggc ttcctgggtc actgatatga gcaatcacaa acgggataaa    3780
tgaccagaca atgagccagc gcactagtgt ctcaccaagc cctattccag gataaatacc    3840
agggcagggc tctgctgcat ggggacgggg agctgccctc ctgagctggc caagcctctc    3900
agtgcaagac ggcaagccct ggctccagca gcacggcagt ccgtgttttc agggcagggg    3960
gagggggcgc tggctggttc tcctgtcccc actcccacca aacactgccc caccgtgaat    4020
ggttcagagt ggagcagaca ggcctgaaac tttgcagagg gtgtccccac atctgattcc    4080
aggactggtt ttctcaggca ttcaagccga cagagtgaca gcagtcccac tcacacatgc    4140
agttttctag ttccaccaat cttgccttct gacttgatct gagagtccca ggttcttctt    4200
ctgaacaagg gctgttgtga gggtgaagcg ggacagtgct taagtgctta acatatagtg    4260
aaagctcaac taatagtagc tactattatt attttttatac atagaaaaag ctttgcactt    4320
gggaatttca atttgtaaat gataaataat tcatggtaag catttcaagg catcacaaac    4380
```

```
atttgctgcc ctgttttatc aaggtaattt cagttcggaa gcagatgtat aatataattg    4440
aagttagtgc cctgctcctg cccatccaca ggtgcctccc cacctctacc cccgtggagt    4500
tacaatcttc tgtatgtttt gtttactttt ttagttttg agataaggtc ttgctcagtc    4560
acccaggttg gagtgcagtg gtgcaatctt ggctcattgc agcctcaacc tcccaggctc    4620
aagcgatcct ccgcctcagc ctcctgagta gctgggaata cgggcacatg gaccatgccc    4680
agctaattgt tttatttttt ctttgtagag atggagtctc cctatgttgc ccaggctggt    4740
ctcaaacttc ctgtgctcaa gttatcctcc tgccttagct tcccaaagtg ctgggattac    4800
aggtgtgagc caccgtgcct gacccctgtg tgtcttatag ccaaggcagc tgttgtacat    4860
tacacttgac ttcttcaggc caagccttcc tatcccggag aattgttact ctgcatttat    4920
gctcttcatc agtgttcaat acccaaattt ttcccaccac gtttgtagcc ctgcactgtg    4980
gttgttcctc tgaggctgtg cacatcactt aacagccaca ccattcattt ggcttcaatg    5040
tcaggcagaa ctgtcaggaa aaagtttcat gacacctaga aagcaattca agtgggaaaa    5100
agaatacagg gttaacaaat gtaggccacg ttcccaagag ttacttcagc aacaaagaag    5160
actttcaaaa cattaaattc cactggaagc ctttgagaca gggacttcca cacacagaac    5220
acacgaaaag tttaggaggg ccaaaagttt attttatt caagacattt gctcaggctg    5280
atctagatgg tattttttt tttcaggtat tttaagtatg ataacaacct tcagtttttc    5340
acctcttggc tgttccattc agccttttcc agtagctcag ggccagacac tgaccccag    5400 agatttctgc ttggacaaca gcccctggt cacatgagac atcttttctg atattttgca    5460
tttgatgttc ttaggttatt tcggacacaa attatcagag tcactcaact tttaatcatg    5520
ttttgatggt ccaaaattcc atttaaaaac aaggtcggca actccttta tctctcttag    5580 gaaatcaaag agcaggaggt tgtggacaaa gtcatggaaa cactggacaa tgatggagac    5640
ggcgaatgtg acttccagga attcatggcc tttgttgcca tggttactac tgcctgccac    5700
gagttctttg aacatgagtg agattagaaa gcagccaaac cttcctgta acagagacgg    5760 tcatgcaaga aagcagacag caagggcttg cagcctagta ggagctgagc tttccagccg    5820
tgttgtagct aattaggaag cttgatttgc tttgtgattg aaaaattgaa aacctctttc    5880
caaaggctgt tttaacggcc tgcatcattc tttctgctat attaggcctg tgtgtaagct    5940
gactggcccc agggactctt gttaacagta acttaggagt caggtctcag tgataaagcg    6000
tgcaccgtgc agcccgccat ggcgtgtag accctaaccc ggagggaacc ctgactacag    6060
aaattacccc ggggcaccct taaaacttcc actacctta aaaacaaag ccttatccag    6120 cattatttga aaacactgct gttctttaaa tgcgttcctc atccatgcag ataacagctg    6180
gttggccggt gtggccctgc aagggcgtgg tggcttcggc ctgcttcccg ggatgcgcct    6240
gatcaccagg tgaacgctca gcgctggcag cgctcctgga aaaagcaact ccatcagaac    6300
tcgcaatccg agccagctct gggggctcca gcgtggcctc cgtgacccat gcgattcaag    6360
tcgcggctgc aggatccttg cctccaacgt gcctccagca catgcggctt ccgagggcac    6420
taccgggggc tctgagccac cgcgagggcc tgcgttcaat aaaaag                   6466
```

<210> SEQ ID NO 4
<211> LENGTH: 92
<212> TYPE: PRT
<213> ORGANISM: Homo sapiens

<400> SEQUENCE: 4

Met Ser Glu Leu Glu Lys Ala Met Val Ala Leu Ile Asp Val Phe His

-continued

```
1               5                   10                  15

Gln Tyr Ser Gly Arg Glu Gly Asp Lys His Lys Leu Lys Lys Ser Glu
            20                  25                  30

Leu Lys Glu Leu Ile Asn Asn Glu Leu Ser His Phe Leu Glu Glu Ile
            35                  40                  45

Lys Glu Gln Glu Val Val Asp Lys Val Met Glu Thr Leu Asp Asn Asp
            50                  55                  60

Gly Asp Gly Glu Cys Asp Phe Gln Glu Phe Met Ala Phe Val Ala Met
65                  70                  75                  80

Val Thr Thr Ala Cys His Glu Phe Phe Glu His Glu
                85                  90
```